United States Patent [19]

Click et al.

[11] Patent Number: 4,596,878

[45] Date of Patent: Jun. 24, 1986

[54] PROCESS FOR THE PRODUCTION OF MALEIC ANHYDRIDE

[75] Inventors: Gaylon T. Click, Pearland; Bruno J. Barone, Houston, both of Tex.

[73] Assignee: Denka Chemical Corporation, Houston, Tex.

[21] Appl. No.: 645,329

[22] Filed: Aug. 29, 1984

Related U.S. Application Data

[62] Division of Ser. No. 561,320, Dec. 14, 1983, Pat. No. 4,515,899.

[51] Int. Cl.$^4$ .............................................. C07D 307/60
[52] U.S. Cl. ...................................... 549/259; 549/260
[58] Field of Search ................ 549/256, 257, 259, 260

[56] References Cited

U.S. PATENT DOCUMENTS

| | | | |
|---|---|---|---|
| 3,296,282 | 1/1967 | Kerr | 549/25 |
| 4,020,174 | 4/1977 | Partenheimer | 549/259 |
| 4,094,816 | 6/1978 | Partenheimer | 502/35 |

FOREIGN PATENT DOCUMENTS 1464198  2/1977  United Kingdom .

*Primary Examiner*—Henry R. Jiles
*Assistant Examiner*—Bernard I. Dentz
*Attorney, Agent, or Firm*—Kenneth H. Johnson

[57] ABSTRACT

The useful life of vanadium-phosphorus-oxygen (PVO) catalyst in fixed bed reactors can be substantially extended by treatment with a phosphorus compound followed by steam treatment. The PVO catalysts may be treated with steam after long periods (months) of only phosphorus compound treatment and the benefit of the present invention obtained or the phosphorus and steam treatments may be of only a few hours duration and sequential. In extending the useful life of the PVO catalyst according to the present invention, the temperature profile in the catalyst bed is restored to substantially the same profile as the fresh catalyst.

23 Claims, 8 Drawing Figures

PROCESS FOR THE PRODUCTION OF MALEIC ANHYDRIDE

BACKGROUND OF THE INVENTION

This application is a division of Serial No. 561,320 filed December 14, 1983 and now U.S. Pat. No. 4,515,899.

This invention relates to improvements in the preparation of dicarboxylic acid anhydrides by the vapor phase oxidation of hydrocarbons. More specifically the improvement concerns the regeneration of catalyst for the catalytic oxidation of hydrocarbons to dicarboxylic anhydrides in the presence of a vanadium-phosphorus-oxygen (PVO) catalyst.

It is known that PVO catalysts produce high yields of dicarboxylic anhydrides. Although high yields of dicarboxylic anhydrides have been obtained by such procedures, it has been found that the yield of product diminishes with time due to a reduction in the selectivity of the catalyst. Several methods of regenerating the PVO catalyst in situ have been devised.

Two early patents in this area are U.S. Pat. Nos. 3,296,282 and 3,474,041 issued to Ralph O. Kerr. These patents disclose that the PVO catalyst may be regenerated and stabilized by adding specified organo-phosphorus compounds to the catalyst The organo-phosphorus compound may be added with or without the hydrocarbon, either intermittently or continuously It was found that during the use of the catalysts a portion of the phosphorus is removed from the catalyst, thereby disrupting the initial ratio of P:V in the catalyst, and the added phosphorus compound replaced a portion of the lost phosphorus to thereby maintain the catalyst close to its original selectivity and extending the useful life of the catalyst. A similar approach was disclosed in British Patent Specification No. 1,291,354, and U.S. Pat. Nos. 3,906,008 and 3,975,407.

Another approach to the same problem, i.e., the disruption of the ratio of P to V by phosphorus loss in the catalyst, is the removal of some of the vanadium A process using this method is disclosed in U S Pat. Nos. 4,020,174; 4,098,807 and 4,094,816 issued to Partenheimer. The use of various organic and inorganic halogen compounds are disclosed to regenerate the catalyst. After treatment with alkyl halides, the patents suggest a steam treatment to cause a water gas reaction to remove residual carbon deposited by the alkyl halide. In the U.S. Pat. No. 4,098,807 patent the formation of the volatile vanadium halide is specifically noted, and the patentee discloses the unsuitability of $PCl_3$ or $PCL_5$ for the regeneration, because of the deposits of phosphorus onto the catalyst.

U.S. Pat. No. 4,111,832 discloses the use of aqueous ammonia and/or amine to at least partially dissolve the catalyst and thereafter redepositing the catalytic components from the solution.

British Patent Specification No. 1,464,198 discloses the regeneration of PVO oxidation catalysts by the addition of alkyl esters of orthophosphoric acid.

British Patent Specification No. 1,439,489 discloses the regeneration of PVO catalyst with a reducing agent such as hydrogen, carbon monoxide, methane or hydrogen sulfide.

The present invention is concerned with the regenerations wherein a phosphorus compound is added to the catalyst to increase selectivity and extend catalyst life. In the past the art has used the term "reactivate" to describe the situation wherein the treatment of the catalyst results in operation of the reaction system thereafter with higher yields than before the treatment, notwithstanding that the "activity" of the catalyst may have been reduced. The term "regeneration" is used herein to mean that a higher yield of product is obtained after treatment. The phosphorus compounds reduce the activity (the term "activity" as used herein, means the ability of the catalyst to convert hydrocarbon at a given temperature) of the catalyst while improving the selectivity. The overall result is that a higher yield (conversions x selectivity) is obtained at a slightly higher operating temperature (higher temperature to boost conversion which is the result of the P addition), i.e., the catalyst is regenerated and is more effective although the activity is actually reduced. The usefulness of this method of PVO catalyst treatment in a commercial maleic anhydride plant with fixed bed reactors is limited by the inability to evenly distribute the phosphorus throughout the catalyst bed.

In practice it has been found that the phosphorus compounds concentrate near the feed end of the catalyst bed. The catalyst, near the feed end of the bed, becomes more selective but less active. The catalyst further from the feed end of the catalyst bed is relatively unaffected, hence this portion remains active but loses selectivity with time in use. The result is that with only a portion of the bed receiving the optimum phosphorus treatment, yield continues to decline. The rate of decline is slower than it would be if no phosphorus treatment were applied, but faster than it would be if even distribution of the phosphorus could be obtained.

Another problem is that the amount of phosphorus addition must be limited; otherwise, the activity of the first part of the bed will become so low that a large portion of the reaction will occur in the last part of the bed. In this case the yield will decline, because the reaction will be occurring in the most nonselective part of the bed. Since the active part of the bed is now effectively shortened, the reactor temperature must be increased to maintain conversion because of the decreased contact time with active catalyst This also leads to a loss in selectivity. It can be appreciated also, that as the site of the principal reaction (indicated by the reaction exotherm or "hot spot" in the temperature profile of the catalyst bed) moves toward the exit end of the catalyst bed, some of the reaction, which was occurring down stream of the exotherm, is actually eliminated because of the shortened bed.

It has now been found that the addition of steam following the addition of phosphorus compounds to a vanadium-phosphorus-oxygen catalyst obviates both of the noted problems. It is believed, the addition of steam to the catalyst bed which has been treated with phosphorus compounds removes a portion of the phosphorus from the feed end of the bed and redistributes it through the remainder of the bed. This results in the entire bed being treated. If a large amount of phosphorus is added or accumulated over a period of time and the feed end of the bed has been rendered inactive, steam treatment will redistribute the phosphorus, which will reduce the activity of the entire bed, but upon further steam treatment, the bed will tend to become active again. This is a proposed mechanism and the scope of the present invention is not intended to be limited thereby.

SUMMARY OF THE INVENTION

According to the present invention, vanadium-phosphorus-oxygen vapor phase partial oxidation catalyst that has declined in selectivity, may be regenerated and stabilized by first treating the catalyst with a phosphorus compound and thereafter treating the catalyst with steam, whereby, the activity of the catalyst is greater than the activity of the catalyst without the steam treatment The term "stabilized" as used herein means that the rate of decline of the yield is slight compared to an unstabilized catalyst.

Thus the present proces which requires both phosphorus treatment and steam treatment is a regeneration, since the conversion at a given temperature, i.e., activity, is still somewhat lower than the untreated catalyst, although the activity is greater after the combined phosphorus/steam treatment than after the phosphorus treatment alone. A true reactivation would be one wherein the activity after treatment is equal to or greater than the untreated catalyst. Although the present process when applied to a fresh catalyst which has shown an initial decline in selectivity in the embodiment wherein the phosphorus treatment and steam treatment are contiguous, may appear in the initial treatment(s) to be reactivation, there will be small and gradual loss in activity (with progressive treatments), albeit at a much slower rate than the phosphorus treatment alone.

In a first embodiment the phosphorus compound treatment may have been over an extended period of time prior to the steam treatment; or in a second embodiment the phosphorus compound treatment and steam treatment may be substantially contiguous, that is, the steam treatment follows immediately after each phosphorus treatment. In the first method of operation only small amounts of phosphorus compound are added to the catalyst either continuously or intermittently, such that the deactivating effect of phosphorus is very small, although it may be cumulative over a period of time. In the second method of operation, a larger amount of phosphorus compound is added over a relatively short time period which causes severe deactivation of the catalyst and it is necessary to follow soon after with a steam treatment to reactivate the catalyst. It should be appreciated that although phosphorus has a deactivating effect (as described herein) that it also enhances and improves the selectivity of the catalyst to the anhydride product. Thus, the addition of phosphorus to the catalyst is beneficial and the treatment with steam extends and enhances the benefits from the phosphorus. In both methods of regeneration the hydrocarbon may be present or absent during the treatment with the phosphorus compound or the steam.

The benefit of the first method extends to existing commercial reactors wherein phosphorus compound addition as taught in the art has been utilized with the known slow decline in selectivity. The life of the catalyst can be extended by combining the steam treatment as described with the phosphorus treatment whereby it is believed the phosphorus is more uniformly redistributed throughout the catalyst.

In a preferred embodiment, the phosphorus compound treatment will be followed substantially sequentially by steam treatment when catalyst selectivity has declined. Using this embodiment the deactivating effect of phosphorus is somewhat overcome or at least moderated. In this mode, it is believed the catalyst may be kept near its original selectivity for an extended period of time and perhaps indefinitely.

The treatment or addition of phosphorus compounds and/or steam to the catalyst is obtained by contacting the catalyst in situ in the reactor with the designated materials. In addition to the hydrocarbons which may be present, air may be present and in the case where phosphorus compound is added in the absence of hydrocarbon, a carrier gas such as air or nitrogen may be used.

DETAILED DESCRIPTION OF THE INVENTION

Figure 1:
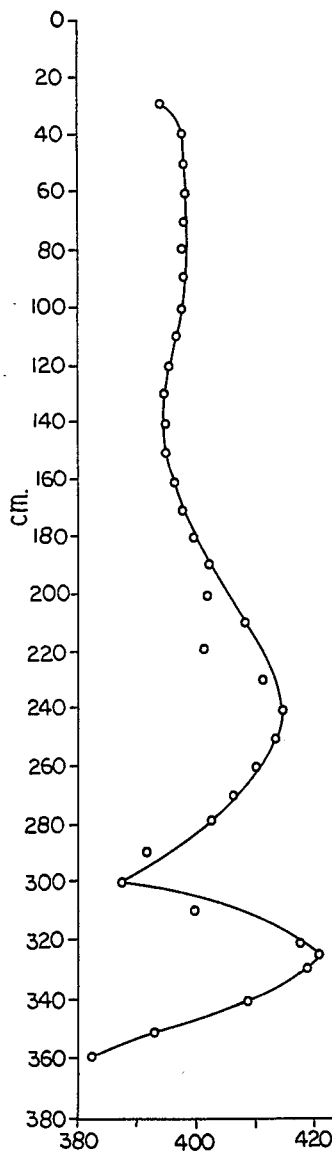
FIGS. 1–8 depicts the temperature profile for the catalyst bed in the runs described in TABLE III (Example 3).

Broadly the vanadium-phosphorus-oxygen catalysts to be regenerated according to this invention comprise vanadium, ,hposphorus and oxygen combined as a complex. The overall ratio of vanadium to phosphorus in the catalyst bed to be treated will have an atomic ratio of about ½ to 3 atoms of phosphorus per atom of vanadium. The vanadium-phosphorus-oxygen catalyst may also contain various stabilizers and metal additives, generally in percents of less than 15 weight percent based on the total weight of vanadium and phosphorus The atomic ratio of oxygen to the remaining components of the catalyst, when the catalyst is in the process of being used to catalyze the oxidation, is difficult to determine and is probably not constant due to the competing reactions of oxidation and reduction taking place during the reaction at high temperatures. The overall ratio of oxygen to the cOmbined atoms of vanadium and phosphorus at room temperature would be such as about 2 to 6 atoms of oxygen per the combined atoms of vanadium and phosphorus At any rate the catalyst is present during the reaction as an oxide of vanadium and phosphorus.

The catalytic material from which the catalyst structure is made is a vanadium-phosphorus-oxygen complex type catalyst for the conversion of hydrocarbons to the corresponding anhydride. The catalyst usually contains at least one modifying component, Me, which is a metal (including the rare earth metals) an alkali, alkaline earth metal, or mixture thereof The precise structure of the present complex catalyst has not been determined; however, a preferred complex may be represented by formula $VP_aMe_bO_x$ wherein Me is the modifying component, a is 0.90 to 1.3, b is 0.001 or greater, preferably 0.005 to 0.4. The representation is not an empirical formula and has no significance other than representing the atom ratio of the active metal components of the catalyst. The x, in fact, has no determinate value and can vary widely, depending on the combinations within the complex. That there is oxygen present is known and the $O_x$ is representative of this.

The Me component as well as the base composition and ratios of components are all well known as described in infinite detail in the art noted herein. The composition of the catalytic component is not the subject of the present invention although it is an integral part of the invention.

Among the various Me components which have been used either alone or in combination with each other are metal and metaloids from Groups Ia, Ib, IIa, IIb, IIIa, IIIb, IVa, IVb, Va, the 4th period of VIIIb, and the rare earths of the Periodic Table of elements. Some specific Me components are Cu, Ag, Zn, Cd, Al, Ga, In, Sc, Y, La, Ge, Sn, Pb Ti, Zr, Sb, Bi, As, Fe, Co, Ni, Ce, Pr, Nd, Cr, Li, Na, K, Rb, Fr, Nb, Te, W, Pd, Mn, Mo, Re, Sm, Hf, Ta, Th, U, Sn, B, Si, Mg, Ba, Tb and Eu.

The Me components are variously described as stabilizers, promoters, modifiers or the like. Regardless of the characterization the Me components are a part of the catalyst, in that they effect the performance thereof in the oxidation of hydrocarbons.

In regard to normal butanes some more preferred Me Components are Cu, Mo, Ni, Co, Cr, Nd, Ce, Ba, Y, Sm, Te, Zr, W, Pd, Ag, Mn, Zn, Re, La, Hf, Ta, Th, U, Eu, Nb, Ru, Li, Mg, B and Si.

Although the catalyst may be produced with carriers or diluents, it is not preferable or desirable to do so if the feed is normal butane, since normal butane requires a greater excitation, than for example n-butene. The presence of carriers or diluents will not effect the structure, but such a catalyst may have low yields and productions from alkanes. It can be readily appreciated that the presence of the greatest number of active catalytic sites o the catalyst structure is the desirable condition for a butane oxidation catalyst.

Some of the more effective catalysts in terms of productivity and stability are those with few components in addition to P-V-O such as Zn, Li and/or Si, such as disclosed and noted above in commonly owned U.S. Pat. No. 4,251,390. The resultant catalyst complex is characterized as a mixed oxide, however, the structure of the complex has not been determined but may be conveniently represented by a formula such as $V P Zn_e Si_c Li_d O_x$ where a is 0.90 to 1.3, e is 0.005 to 0.2, c is 0 to 0.3 nd d is 0 to 0.15. As noted above, this representation is not an empirical formula and has no significance other than representing the atom ratio of the components of the catalyst.

It has been found that lower ratios of zinc/vanadium produce the most stable catalysts and compositions containing Zn/V mole ratio in the range of 0.01 to 0.07 are preferred.

The phosphorus is generally present in these catalysts as well as those of the prior art in the mole ratio of P/V 0.09–1.3/1. Optimum ratios P/V are found to be below 1.22/1 and above 1.0/1.

Basically, all of the methods for producing catalysts for maleic anhydride production employ vanadium in a valence state of less than +5. One method of achieving this is to begin with vanadium in less than the +5 valence state. Another method that is used most widely in the art is to start with vanadium in the +5 state and reduce the valency to less than +5.

Usually the reduced vanadium is obtained by reacting $V_2O_5$ in a solution of HCl and phosphoric acid. A typical catalyst preparation may involve dissolving the vanadium, phosphorus, and other components in a common solvent, such as hot hydrochloric acid and thereafter depositing the solution onto a carrier. The reduced vanadium with a valence of less than 5 is obtained by initially using a vanadium compound with a valence of plus 5 such as $V_2O_5$ and thereafter reducing to the lower valence with, for example, hydrochloric acid during the catalyst preparation to form the vanadium oxysalt, vanadyl chloride, in situ. The vanadium compound is dissolved in a reducing solvent, such as hydrochloric acid, which solvent functions not only to form a solvent for the reaction, but also to reduce the valence of the vanadium compound to a valence of less than 5.

For example, a vanadium compound, a copper compound. a tellurium compound, phosphorus compound and alkali metal compound may be dissolved in any order in a suitable reducing solvent and the formation of the complex allowed to take place. Preferably. the vanadium compound is first dissolved in the solvent and thereafter the phosphorus, copper, tellurium and other metal compounds, if any, are added. The reaction to,- form the complex may be accelerated by the application of heat. The deep blue color of the solution shows the vanadium has an average valence of less than 5. The complex formed may then, without a precipitation step, deposited as a solution onto a carrier and dried; or it may be precipitated, crushed and extruded into pellets or the like. In this procedure, the vanadium has an average valence of less than plus 5, such as about plus 4, at the time it is deposited onto the carrier or precipitated without the carrier. Generally, the average valence of the vanadium will be between about plus 2.5 and 4.6 at the time of the precipitation.

In another method the catalyst is prepared by precipitating the metal compounds, either with or without a carrier, from a colloidal dispersion of the ingredients in an inert liquid. In some instances the catalyst may be deposited as molten metal compounds onto a carrier; however, care must be taken not to vaporize off any of the ingredients such as phosphorus. The catalysts have also been prepared by heating and mixing anhydrous forms of phosphorus acids with vanadium compounds and Me compounds. In any of the methods of preparation, heat may be applied to accelerate the formation of the complex.

Another method of obtaining vanadyl chloride as disclosed by Koppel et al, Ze.it anorg. chem, 45, p. 346–351, 1905, is the reaction of $V_2O_5$ in alcoholic HCl solution. This method has been recommended for the preparation of the vanadium-phosphorus-oxygen oxidation catalyst.for example, by Kerr in U.S. Pat. No. 3,255,211 where the solvent also serves as the reducing agent. Subsequently, U.S. Pat. No. 4,043,943 employed this method of reacting vanadium to prepare the basic vanadium-phosphorus-oxygen catalyst, however, catalyst produced in this manner are known to require a very specific activation procedure in order to be useful as catalyst, as described for example, in U.S. Pat. No. 4,017,521.

In an early series of commonly owned patents, a unique group of vanadium-phosphorus-oxygen, oxidation catalysts, were disclosed, i. e., U.S. Pat. Nos. 3,156,705; 3,156,706; 3,255,211; 3,255,212; 3,255,213; 3,288,721; 3,351,565; 3,366,648; 3,385,796 and 3,484,384. These processes and catalysts proved highly efficient in the oxidation of n-butenes to maleic anhydride. Since the issuance of these pioneer patents, numerous patents have issued with various modifications and improvements over the basic discoveries set forth there, e. g., U.S. Pat. Nos. 3,856,824; 3,862,146; 3,864,280; 3,867,411; 3,888,886; 4,071,539; 4,097,498; 4,105,586; 4,152,338; 4,152,339 and 4,153,577.

In a recently developed procedure disclosed in the commonly assigned U.S. Pat. No. 4,251,390 which is incorporated herein in its entirety, an improved catalyst is that produced from an alcoholic HCl solution of vanadium pentoxide wherein the organic solvent is an alcohol such as isobutyl alcohol and the solubilization of the vanadium is obtained by contacting it with HCl. This is conveniently carried out by passing gaseous HCl through the alcohol having the vanadium pentoxide suspended therein. The vanadium pentoxide reacts with the HCl and is brought into solution as the vanadyl chloride. The completion of the reaction is indicated by the appearance of a dark reddish brown solution. Hydrogen bromide would be about the same as a reducing agent in this system. It has been found that the reaction temperature should be maintained at no greater than 60° C. and preferably less than 55° C. Optimumly active catalysts are the result when the reaction is carried out at temperatures in the range of about 35° C. to 55° C., preferably 40° to 55° C.

To obtain the mixed oxides of vanadium and phosphorus, phosphoric acid of approximately 99% $H_3PO_4$ (90 to 101%) is added, for example, prepared from 85 $H_3PO_4$ and $P_2O_5$ or commercial grades of 105% and 115% phosphoric acid diluted with 85% $H_3PO_4$ and the vanadium compound digested, which is discerned by a change in the color of the solution of a dark blue green. Zinc or other catalyst components are conveniently added along with the phosphoric acid. The alcohol is then stripped off to obtain the dried catalyst.

The point at which the zinc component, lithium component and/or silicon component or other beneficial additives are added is not critical so long as they are present prior to formation of the solid catalyst precipitate. This is conveniently done along with the phosphoric acid addition, thereby assuring the intimate mixing of the catalyst components.

The modifier components are added as the compounds thereof such as acetates, carbonates, chlorides, bromides, oxides, hydroxides, phosphates and the like e. g., zinc chloride, zinc oxide, zinc oxalate, lithium acetate, lithium chloride, lithium bromide, lithium carbonate, lithium oxide, lithium ortho phosphate, tetra ethyl ortho silicate, silicon tetra chloride, or other organo silanes.

Catalysts have been prepared in various shapes and configurations, for example, saddles, discs, spheres, cylinders, tubes, granules and the like. For example, U.S. Pat. No. 2,078,945 discloses hydrosilicate catalyst which may be formed in tubes or solid cylinders, which may then be crushed and screened to provide irregular catalyst shape. U.S. Pat. Nos. 4,178,298 and 4,181,628 both disclose that mixed oxide oxidation catalyst containing vanadium and phosphorus may be employed as pellets, tablets or cylinders. Recently U.S. Pat. No. 4,283,307 disclosed an improved vanadium-phosphorus-oxygen oxidation catalyst comprising tablets having a hole therethrough. that is, the catalyst structure has a bore therethrough. Preferably the height and diameter of the structures are substantially the same, such that the catalyst is substantially a ring of catalytic material.

The term "vanadium-phosphorus-oxygen catalyst" as used herein and in the claims includes and encompasses materials as described above.

The use of this class of catalytic material (as broadly and specifically disclosed) for the partial oxidation of $C_4$-$C_{10}$ hydrocarbons to the corresponding anhydrides is generally recognized. They have been widely considered for the conversion of normal $C_4$ hydrocarbons, both the alkane, n-butane, and alkene, n-butene, for the production of maleic anhydride, which has a wide commercial usage.

The oxidation of the n-C hydrocarbon to maleic anhydride may be accomplished by contacting, e.g., n-butane in low concentrations in oxygen with the described catalyst. Air is entirely satisfactory as a source of oxygen, but synthetic mixtures of oxygen and diluent gases, such as nitrogen, also may be employed. Air enriched with oxygen may be employed.

The gaseous feed stream to the standard tubular oxidation reactors normally will contain air and about 0.5 to about 2.5 mole percent hydrocarbons such as n-butane. About 1 0 to about 2.0 mole percent of the n-$C_4$ hydrocarbon are satisfactory for optimum yield of produc for the process of this invention. Although higher concentrations may be employed, explosive hazards may be encountered except in fluidized bed reactors where concentrations of up to about 4 or 5 mole % can be used without explosive hazard. Lower concentrations of $C_4$, less than about one percent, of course, will reduce the total yields obtained at equivalent flow rates and thus are not normally economically employed.

The flow rate of the gaseous stream through the reactor may be varied within rather wide limits but a preferred range of operation is at the rate of about 50 to 300 grams of $C_4$ per liter of catalyst per hour and more preferably about 100 to about 250 grams of $C_4$ per liter of catalyst per hour. Residence times of the gas stream will normally be less than about 4 seconds, more preferably less than about one second, and down to a rate where less efficient operations are obtained. The flow rates and residence times are calculated at standard conditions of 760 mm. of mercury and at 25° C. A preferred feed for the conversion to maleic anhydride is a n-$C_4$ hydrocarbon comprising a predominant amount of n-butane and more preferably at least 70 mole percent n-butane.

A variety of reactors will be found to be useful and multiple tube heat exchanger type reactors are quite satisfactory. The tubes of such reactors may vary in diameter from about ¼ inch to about 3 inches, and the length may be varied from about 3 to about 10 or more feet. The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Such media may be woods metal, molten sulfur, mercury, molten lead, and the like, but it has been found that eutectic salt baths are completely satisfactory. One such salt bath is a sodium nitrate-sodium nitrite-potassium nitrite eutectic constant temperature mixture. An additional method of temperature control is to use a metal block reactor whereby the metal surrounding the tube acts as a temperature regulating body. As will be recognized by one skilled in the art, the heat exchange medium may be kept at the proper temperature by heat exchangers and the like. The reactor or reaction tubes may be iron, stainless steel, carbon-steel, nickel, glass tubes such as Vycor and the like. Both carbon-steel and nickel tubes have excellent long life under the conditions of the reactions described herein. Normally, the reactors contain a preheat zone of an inert material such as ¼ inch Alundum pellets, inert ceramic balls, nickel balls or chips and like, present at about one-half to one-tenth the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C. above the salt bath temperature. The temperature in the reactor, of course, will also depend to some extent upon the size of the reactor and the $C_4$ concentration. Under usual operating conditions, in a preferred procedure, the temperature in the center of the reactor, measured by thermocouple, is about 300° C. to about 550° C. The range of temperature preferably employed in the reactor, measured as above, should be from about 325° C. to about 515° C. and the best results are ordinarily obtained at temperatures from about 340° C. to about 430° C. Described another way, in terms of salt bath reactors with carbon steel reactor tubes about 1.0 inch in diameter, the salt bath temperature will usually be controlled between about 350° C. to about 550° C. Under normal conditions, the temperature in the reactor ordinarily should not be allowed to go above about 490° C. for extended lengths of time because of decreased yields and possible deactivation of the catalyst.

The reaction may be conducted at atmospheric, super-atmospheric or below atmospheric pressure. The exit pressure will be at least slightly higher than the ambient pressure to insure a positive flow from the reactor. The pressur of the gases must be sufficiently high to overcome e the pressure drop through the reactor.

The maleic anhydride may,be recovered in a number of ways well known to those skilled in the art. For example, the recovery may be by direct condensation or by absorption in suitable media, with subsequent separation and purification of the maleic anhydride.

The phosphorus compounds which are employed for the catalyst treatment preferably are those which are volatile. For the purposes of the present invention a volatile phosphorus compound is a compound having a boiling point or sublimation point at or below the temperature of the treatment and preferably will have a boiling point or sublimation point of no greater than 250° C.

Both organic and inorganic phosphorus compounds may be employed. For example, phosphorus halides, phosphorus oxyhalides, organic phosphines, organic phosphites, organic phosphates, alkyl esters of phosphoric acid and the like including mixtures thereof.

A particularly suitable group of organo-phosphorus compounds to be added to the vanadium-phosphorus-oxygen catalysts according to this invention have a formula selected from the group consisting of:

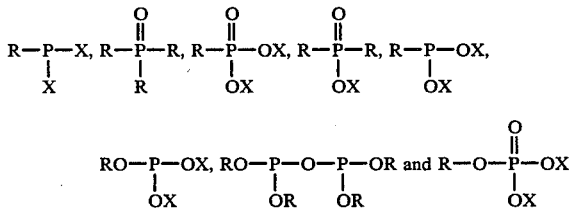

wherein R is phenyl or an alkyl radical having one to six carbon atoms and X is H or R.

Suitable compounds are such as the primary, $RPH_2$, secondary $R_2PH$, and tertiary, $R_3P$, phosphines such as ethyl phosphine; the tertiary phosphine oxides, $R_3PO$, such as tripropyl phosphine oxide; the primary, $RP(O)(OX)_2$, and secondary, $R_2P(O)OX$, phosphonic acids such as benzene phosphonic acid; the esters of the phosphonic acids such as diethyl methanephosphonate; the phosphonous acids, $RPO_2X_2$, such as benzenephosphonous acid and the esters thereof such as the monoethyl ester; the phosphinous acids, $R_2POX$, such as diethyl phosphinous acid and the esters thereof such as the monoethyl ester; the primary, $ROP(OX)_2$, secondary, $(RO)_2POX$, and tertiary, $(RO_3)P$, phosphites such as diethyl phosphite, trimethyl thiophosphite, triethyl phosphite, triisopropyl phosphite, tripropyl phosphite and tributyl phosphite, and the pyrophosphite such as tetraethyl pyrophosphite; and the primary $ROP(O)(OH)_2$, secondary $(RO)_2P(O)OH$ and tertiary $(RO)_3PO$ phosphates such as methyl hydrogen phosphate. The preferred types of phosphorus compounds are the phosphines, phosphine oxides, phosphinites, phosphinite esters, the dialkyl phosphites, the trialkyl phosphites, the tetraalkyl pyrophosphites, the trialkyl phosphates and mixtures thereof.

The phosphites such as the primary, secondary, and tertiary phosphites and thiophosphites such as dimethyl hydrogen phosphite, trimethyl phosphite, triisopropyl phosphite, tributyl phosphite, diethyl thiophosphite, triphenyl phosphite. and tetramethyl pyrophosphite, particularly trimethyl phosphite are preferred.

Organic phosphorus esters which are particularly suitable for the present invention are alkyl esters of orthophosphoric acid having the formula $(R'O)_3P=O$ wherein $R'$ is hydrogen or an alkyl radical having one to six carbon atoms, at least one $R'$ being an alkyl radical. Suitable phosphoric acid esters are, for example, dimethyl hydrogen phosphate, trimethyl phosphate, ethyl dihydrogen phosphate, diethyl hydrogen phosphate, triethyl phosphate, dipropyl hydrogen phosphate, triisopropyl phosphate, butyl dihydrogen phosphate, diisobutyl hydrogen phosphate, and tributyl phosphate. Trimethyl phosphate is preferred.

Suitable inorganic phosphorus compounds include phosphorus tribromide, phosphorus dichloride, phosphorus trichloride, phosphorus dichloride trifluoride, phosphorus oxybromide. phosphorus oxydibromide chloride, phosphorus oxybromide dichloride, phosphorus oxychloride, and phosphorus sesqui oxide.

A particularly suitable group of inorganic phosphorus compounds are phosphorus halides of the formula $PX'_n$ wherein $X'$ is Cl, Br, I or F and n is 3 to 5.

The phosphorus compounds can be added to the vanadium-phosphorus-oxygen catalysts in a number of different ways. Preferably the vanadium-phosphorus-oxygen catalyst will first be used for the oxidation of hydrocarbons to dicarboxylic anhydride for a period of time until the yield of dicarboxylic anhydride diminishes. The phosphorus compound may then be added. The phosphorus compound addition may be accomplished either with or without the flows of hydrocarbon and/or oxygen continued. Steam may be used after each phosphorus compound addition or after multiple or long term phosphorus compound additions as described herein.

Another method for the addition of phosphorus compounds to the vanadium-phosphorus-oxygen catalyst is by the continuous or intermittent addition of the phosphorus compound to the gaseous stream of hydrocarbons and oxygen containing gases entering the reactor. By such a technique, the selectivity of the vanadium-phosphorus-oxygen catalyst is maintained through continuous regeneration or stabilization of phosphorus until the gradual decline in catalyst selectivity is such that the steam treatment is required. An advantage of this procedure is that the production of dicarboxylic anhydride does not have to be interrupted.

Still another method for the addition of the phosphorus compound to the vanadium-phosphorus-oxygen catalyst is by the addition of the organo-phosphorus compound in liquid phase by pouring the phosphorus compound over the catalyst to be regenerated followed by steam as described.

Thus, the phosphorus compound may be added to the vanadium-phosphorus-oxygen catalyst by a variety of methods such as adding phosphorus compound as a liquid or gas. Other techniques such as the use of an aerosol to convey the phosphorus compound are also satisfactory. Suspensions or colloidal solutions of the phosphorus compounds may be employed. Solvents for the phosphorus compound may be included. The phosphorus compound may be added to the hydrocarbon, the oxygen containing gas or via a diluent gas such as nitrogen. The overall temperature range for the addition of the phosphorus compound suitably will be from about 0° C. to 600° C., depending upon the particular compound selected and the method of addition. However, the preferred temperature of the vanadium-phosphorus-oxygen catalyst at the time of addition of the phosphorus compound will be at least 325° C. with still better results being obtained at a catalyst temperature of at least 375° C. The upper limits of the temperature of the catalyst during regeneration will suitably be about 550° C. or 600° C., or perhaps higher for momentary periods of time. The pressure during the addition may be atmospheric, sub-atmospheric or super-atmospheric. The conditions of concentration, temperature and pressure should be adjusted to permit optimum contact of the phosphorus compound with the vanadium-phosphorus-oxygen catalyst.

The amount of phosphorus compound added may be varied depending upon such factors as the age of the catalyst, the temperature at which the catalyst has been operated, the composition of the vanadium-phosphorus-oxygen catalyst and so forth. When the phosphorus compound is continuously added to the gaseous stream entering the reactor, the quantity is generally relatively small such as at least about 0.00004 mole of phosphorus compound added per gram atom of vanadium in the catalyst per day, such as at an average rate of 0.00014 gram mole per day per gram atom of vanadium, or based on the hydrocarbon entering the reactor about 0.000005 to 0.0001 mole of the phosphorus compound per mole of hydrocarbon. Preferred amounts are about 0.00001 to 0.00005 mole of the phosphorus compound per mole of the hydrocarbon such as butane.or butene. As pointed out above, the addition may be either intermittent or continuous. Of course, even if the phosphorus compound is added continuously, it is not necessary to add the phosphorus compound at a constant rate. In the method of phosphorus addition to the catalyst wherein the hydrocarbon flow is stopped, the amount of phosphorus compound added will generally be from about 0.001 to 0.30 gram moles of phosphorus compound per gram atom of vanadium in the catalyst, and preferably will be from or about 0.02 to 0.10 gram moles of phosphorus compound per gram atom of vanadium in the catalyst.

The steam is added to the PVO catalysts after the addition of the phosphorus compound The length of time the phosphorus compound is added to the PVO catalysts is not critical, that is, the phosphorus compound may have been added over a period of hours, days, months or years prior to the treatment with steam. It is also not necessary that the hydrocarbon feed and oxygen be terminated during the steam treatment, although as described above the steam treatment will tend to distribute the phosphorus along the bed, and at least initially the activity of the bed will drop substantially.

In one embodiment the PVO catalyst bed is treated with the phosphorus compound as described above and in the art to improve selectivity until the phosphorus treatment alone fails to produce an improvement in catalyst selectivity or the improvement is such that the catalyst activity is not adequate or as desired for commercial operation, as noted it may be after several years on stream. The steam treatment is preferably conducted for a sufficient period of time and in a sufficient amount to produce a higher activity in the PVO catalyst greater than that prior to the steam treatment Generally the steam treatment will be for several hours, e.g. 1 to 12 hours. As described earlier, it is believed, the steam causes the phosphorus deposited on the upstream catalyst to be moved through the bed to improve selectivity along the entire bed and reduce the amount of phosphorus on the upstream end of the bed, where it has a catalyst killing effect in excess. Thus, the amount of steam and the duration of the steam treatment must be less than to remove all of the phosphorus or to remove phosphorus to a level below its beneficial level. Since the PVO catalyst and the effect of phosphorus compounds is not fully understood by the art, at this time, it is not possible to provide quantitative measures of the amounts of steam and the duration required. It has been found that in regard to a fixed bed, tubular reactor, a pilot tube corresponding to the commercial unit, substantially duplicating the commercial unit operation, including phosphorus treatment can be used to determine op imum conditions of steam treatment for a given PVO catalyst. This procedure involves treating the pilot tub incrementally with steam followed by running the reaction and determining the bed profile (temperature, hot spot, selectivity, etc.) to obtain the optimum steam treatment.

Those factors which affect the steam treatment are (1) the temperature of the reactor, (2) the amount of steam and (3) the amount of phosphorus deposited on the catalyst. Higher temperatures in the reactor require shorter periods of steam treatment. Similarly larger volumes of steam (e.g., not diluted with hydrocarbons, air or inerts) require shorter steam treatment. The steam may be superheated and the pressure may be atmospheric, super- or subatmospheric. Generally the temperature of the reactor during the steam treatment will be in the range of 300° C. to 600° C., preferably 400° C. to 440° C. It would appear that the total volume of steam used (whether in a sin9le treatment or in series of steam treatments, alternated for example with hydrocarbon oxidation) will equal at least 20% by weight of the catalyst being treated. The steam is applied as a flow through the the catalyst bed. Static steam treatment has not been observed to be beneficial. The maximum amount of steam employed in the treatment is determined by the above factors, preferably the maximum amount of steam, i e., the total in single steam treatment without intervening phosphorus treatment, is that to obtain maximum regeneration of the catalyst.

In another embodiment of the present process a massive treatment of the catalyst with a phosphorus compound is carried out, followed by the steam treatment to reactivate the catalyst, i.e., increase the activity above that after the phosphorus treatment alone. This procedure has as an advantage, the assurance that optimum phosphorus is present at all times to provide the improved selectivity along the bed after steam treatment. Whereas steam treating a bed that has been on stream for example, for a year or more with a continuous phosphorus compound treatment, will result in an improvement. but possibly not the optimum possible.

In the following examples, two types of reactors were employed. The results of the tests in the two reactors are qualitatively comparable, i. e., an increase in maleic anhydride yield in the smaller equipment will be reflected in the larger equipment, although the absolute numbers may differ.

REACTORS

The reactors are 3 to 12 foot tubes varying from $\frac{3}{4}$ to 1 $\frac{1}{4}$ inch inside diameter as specified below. For example, a 3 foot carbon steel tube, $\frac{3}{4}$ inch inside diameter, reactor employed 300 milliliters of catalyst packed with inert $\frac{1}{4}$ inch Alundum pellets on top of the catalyst material to a height $\frac{1}{3}$ of the height of the catalyst. For each reactor, the catalyst material and inerts above are:

| Length Diameter | Flow | Ml Catalyst | Inert Packing | |
|---|---|---|---|---|
| 3' × $\frac{3}{4}$' | Down | 300 | $\frac{1}{4}$" | Alundum* Pellets, Top |
| | | | $\frac{1}{3}$ | Catalyst Bed |
| | | | $\frac{1}{4}$" | Alundum* Pellets |
| 12' × 1" | Up | 950 | 12" | At Bottom |
| | | | 6" | At Top |

*Fused Silica Alumina

The reactors were encased in a 7% sodium nitrate-40% sodium nitrite-53% potassium nitrite eutectic mixture constant temperature salt bath. The reactor was slowly warmed to 400° C. (250°-270° C. air passing over catalyst) while passing a gas stream containing 0.5 to 0.7 mole percent n-butane and air over the catalyst beginning at about 280° C. The reactor outlet was maintained at 1 psig (or as indicated). After the reactor had reached 400° C., the catalyst was aged by passing the n-butane - air mixture therethrough for 24 hours. The n-butane - air and temperature was increased to obtain a maximum throughput. The n-butane in the feed is increased to 1.0-1.5 mole percent to obtain 80-90% conversion. The salt bath is operated at a maximum of 425° C. The maximum throughput is achieved in relation to the maximum salt bath temperature and maximum hot spot of about 450° C. The hot spot is determined by a probe through the center of the catalyst bed. The temperature of the salt bath can be adjusted to achieve the desired relationship between the conversion and flow rates of the n-C4 - air mixture. The flow rate is adjusted to about 85% conversion and the temperature relations given above. Generally, flow rates of about 30 to 75 gram of hydrocarbon feed per liter hour are used. The exit gases were cooled to about 55°-60° C. at about $\frac{1}{2}$ psig. Under these conditions, about 30-50% of the maleic anhydride condenses out of the gas stream. A water scrubber recovery and subsequent dehydration and fractionation wer used to recover and purify the remaining maleic - anhydride in the gas stream after condensation. The combined maleic anhydride recovered is purified and recovered at a temperature of about 140°-150° C. overhead and 145° C. bottoms temperatures in a fractionator. The purified product had a purity of 99.9+ percent maleic anhydride.

EXAMPLE 1

In this example, a commercial PVO catalyst in use for about 26 months for the production of maleic anhydride (MAN) from n-butane in a commercial reactor was removed and reloaded in a 3 foot unit. The catalyst may be described as 3/16"×3/16" solid tablets originally containing PVO and a small amount of Zn as described in U. S. Pat. No. 4,251,390. The commercial reactor contains 12 foot long tubes and the portion of the catalyst used in the present test was the upper 300 ml of the first 450 ml of catalyst on the feed end of one tube of the reactor. During about the last 20 months the catalyst was on stream in the commercial multitube reactor about 1 to 1.5 liters of trimethyl phosphite was added daily. The specific run conditions are set out in TABLE I. Referring to TABLE I it can be seen that after the reloaded catalyst was brought on stream in the 3 foot reactor and lined out as described above, the selectivity to MAN was 41.1 mole%, conversion 74.6% and the yield (weight%) was 51.7. After treatment with steam according to the present invention selectivity had increased to 46.4%, conversion to 78% and the yield to 61.2 wt% MAN.

Following that a large dose of PCl was charged to the reactor followed by steam. The selectivity was high, however, as described above, the activity was still reduced because the phosphorus had not been distributed through the catalyst bed. Further steam treatment produced a more active catalyst with yield (wt%) of 71.+%. Treatment according to the present invention raised the selectivity and yield to high levels. By repeating the treatment with a phosphorus compound followed with steam the useful life of the catalyst is substantially extended.

EXAMPLE 2

In this set of runs the same catalyst as described in Example 1 was used in the 3 foot reactor. This catalyst was the first 300 ml of catalyst on the feed end of one tube of a commercial reactor (a different tube than that of Example 1 same reactor). The test reactor was on stream for 42 days. The conditions and manner of treatment are set out in TABLE II. The principal distinction from Example 1 is the use of nitrogen as the carrier gas for PCl$_3$. The results show the same type of regeneration as in Example 1.

EXAMPLE 3

The catalyst was a freshly prepared PVO catalyst of the type disclosed in U. S. Pat. No. 4,251.390 with a bore through the tablets ( U.S. Pat. No. 4,283.307). The reactor used was the 12 foot 1 inch diameter reactor with a 10.5 foot catalyst bed. The catalyst was 3/16"×3/16" tablets with a hollow core. The specific conditions and results are set out in TABLE III. Since the catalyst was fresh it was on stream 1562 hours when a drop in selectivity and activity (drop in activity shown by increased reactor temperature to maintain conversion). At this time a large dose of trimethyl phosphite (vapor) in air was added to the catalyst bed, which resulted in a drop in activity as expected. Subsequent treatments with steam brought the catalyst activity back up and restored its selectivity to close to the original selectivity.

Figure 2:
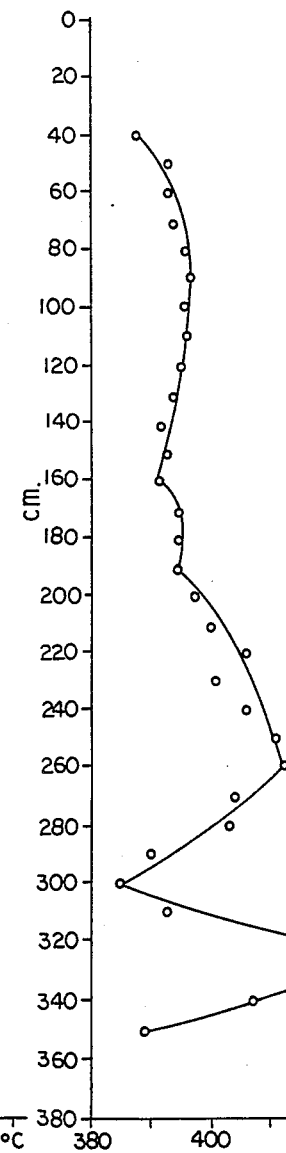
Figure 3:
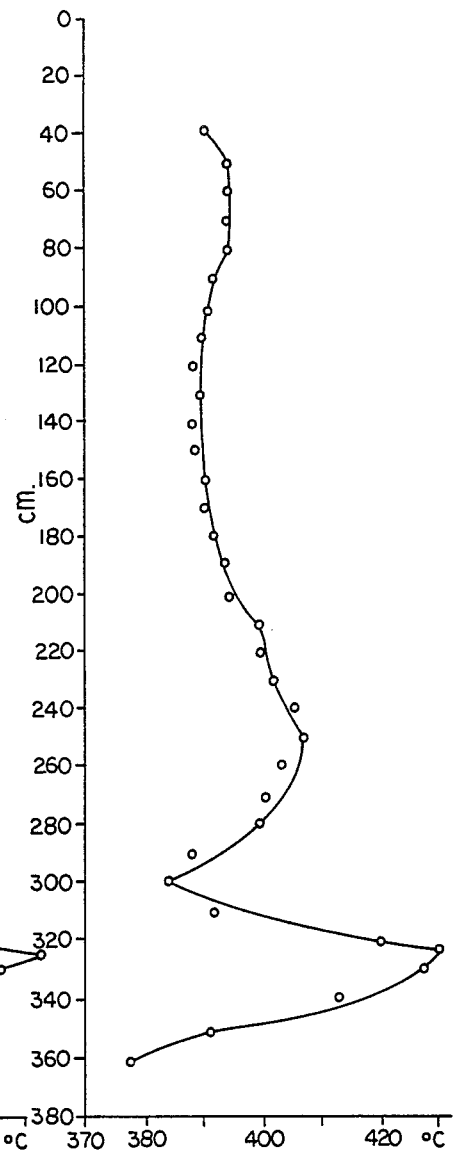
Figure 4:
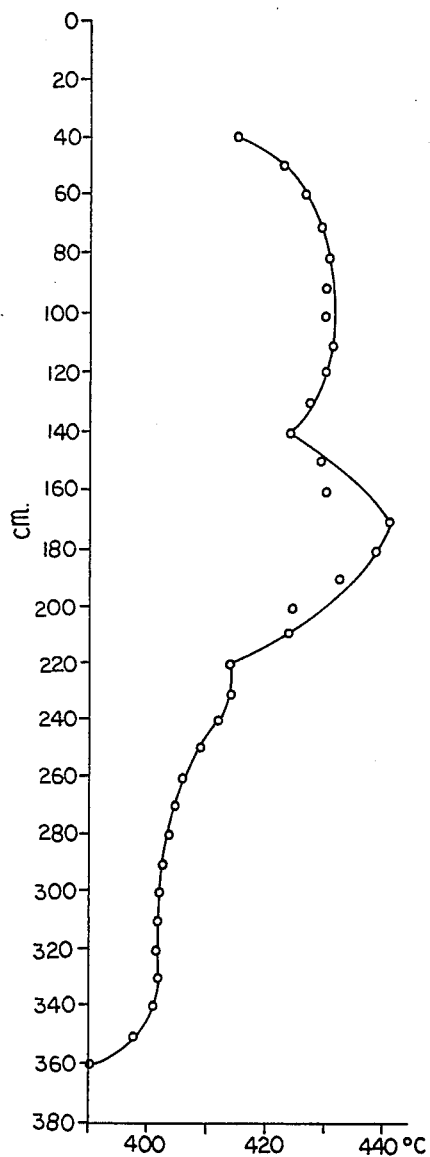
Figure 5:
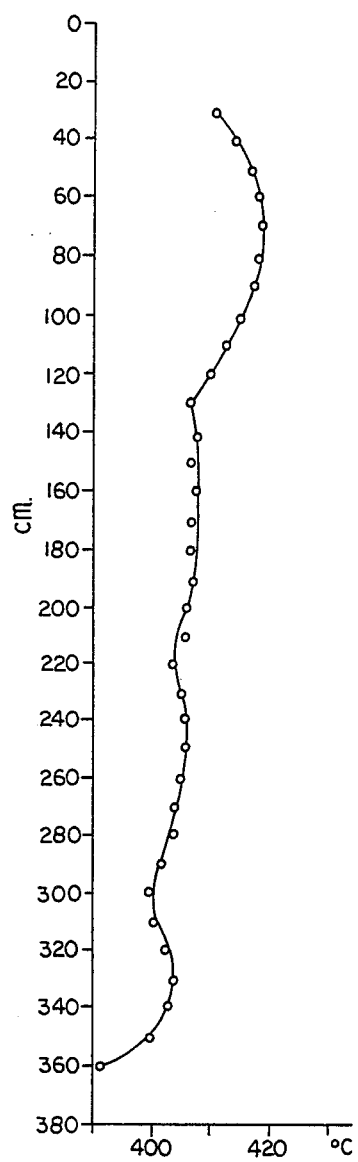
Figure 6:
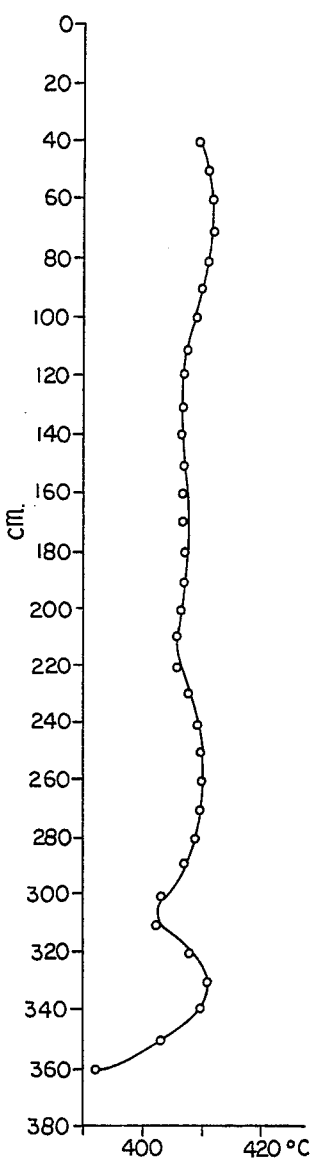
Figure 7:
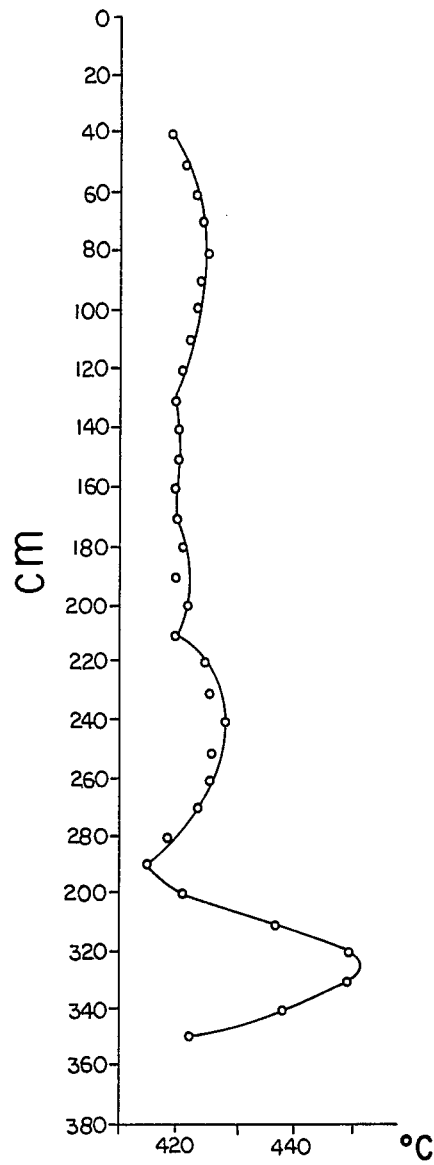
Figure 8:
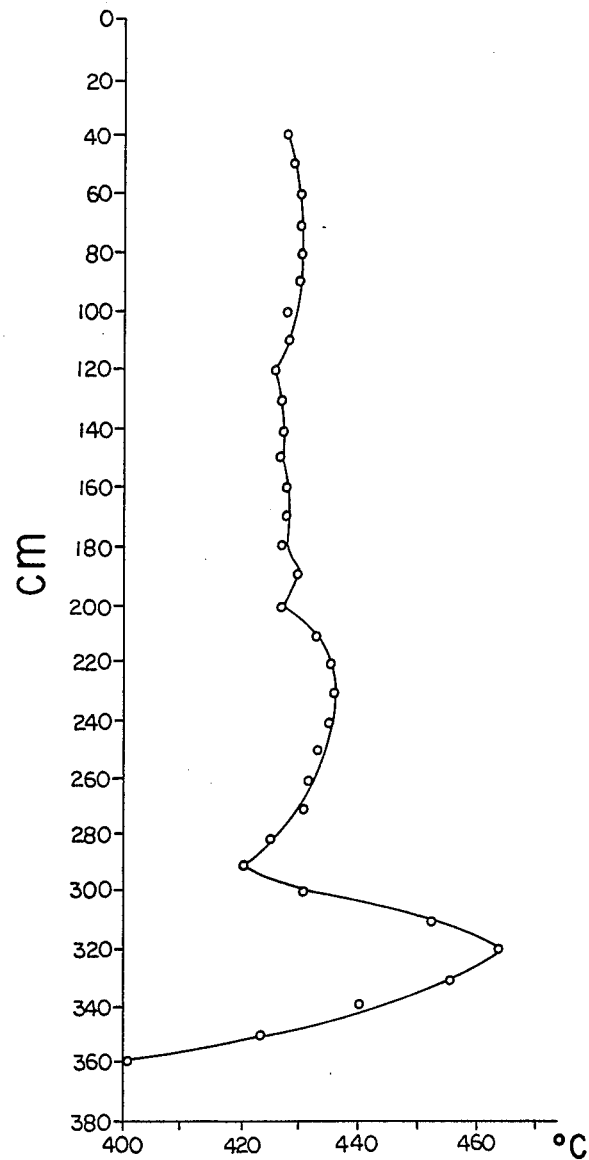

The temperature profile in the reactor is shown for each reported set of conditions and results in TABLE III, in FIGS. 1-8. The reactant flow is upward. FIGS. 1-3 show the exotherm near the front of the bed, where as discussed earlier, it is desirable. FIG. 4 shows how the phosphorus compound has deactivated the front portion of the bed and moved the exotherm further into the bed. The first steam treatment moved the phosphorus from the front end and substantially reduced the activity of the entire bed in the same manner as the front end had been deactivated by the phosphorus, although the selectivity was very high (FIG. 5). The second steam treatment removed some of the excess phosphorus from the front of the bed and a slight exotherm is evident (FIG. 6). A third steam treatment further displaced phosphorus and a true exotherm at the front of the bed with a good yield for the unit is obtained four hours after the steam treatment (FIG. 7). After the system had lined out at 1616 hours on stream the yield was back up to 83 wt% (FIG. 8) with the exotherm at the front of the bed.

In prior operations smaller amounts of the phosphorus compound would have been used to increase selectivity as the yield declined, however, over a period of time the cumulative effect would have been to force the exotherm deeper into the bed as shown in the FIGS. and even with increased selectivity yield would decline. as shown by the first run in Example 1 where a commercial catalyst was at low yield after about 20 months of phosphorus treatment only. The present invention will add months and possibly years to the catalyst life. Theoretically, it would appear the catalyst life could be extended indefinitely, however, other factors. such as plugging of the pores in the catalyst particles, fatigue, and attrition and possible reactor upsets play a part in catalyst life and only long term commercial operation will determine the final length of time the catalyst can be used.

TABLE I

| Date | Temperature, °C. Salt | Temperature, °C. Hot Spot | Butene Feed Mole % | GHSV Hr$^{-1}$ | On-Stream Hrs. | Butane Conv. Mole % | MAN Select. Mole % | MAN Yield Mole % | MAN Yield Wt. % |
|---|---|---|---|---|---|---|---|---|---|
| 14 | 410 | 439 | 1.230 | 1500 | 191 | 74.6 | 41.1 | 30.6 | 51.7 |
| Steamed for 4.0 Hours at 410° C. with 40 wt. % steam in air (500 hr$^{-1}$ G) | | | | | | | | | |
| 15 | 400 | 438 | 1.291 | 1500 | 216 | 78.0 | 46.4 | 36.2 | 61.2 |
| Treated with 1.5 ml PCl$_3$ in air (500 hr$^{-1}$ GHSV) at 400° C. | | | | | | | | | |
| Steamed for 2.0 hours at 400° C. with 40 wt. % steam in air (500 hrs$^{-1}$ GHSV) | | | | | | | | | |
| 15 | 400 | 415 | 1.188 | 1500 | 220 | 44.3 | 79.0 | 35.0 | 59.2 |
| Steam Treatment Repeated | | | | | | | | | |
| 16 | 400 | 417 | 1.37 | 1500 | 239 | 47.6 | 74.9 | 35.7 | 60.3 |
| Steam Treatment Repeated | | | | | | | | | |
| 17 | 400 | 420 | 1.067 | 1500 | 262 | 62.9 | 67.2 | 42.3 | 71.5 |
| Steam Treatment Repeated | | | | | | | | | |
| 19 | 400 | 423 | 1.271 | 1500 | 311 | 62.7 | 64.1 | 40.1 | 67.8 |
| 20 | 410 | 448 | 1.44 | 1500 | 340 | 72.1 | 58.4 | 42.2 | 71.3 |
| 23 | 410 | 442 | 1.37 | 1500 | 407 | 70.3 | 60.0 | 42.2 | 71.3 |
| 21 | 415 | 447 | 1.318 | 1500 | 114 | 77.5 | 34.2 | 26.5 | 44.8 |
| Treated with 2.0 ml PCl$_3$ in air (500 hr$^{-1}$ GHSV) at 400° C. | | | | | | | | | |
| Steamed for 8.0 hours with pure steam - no air - at 400° C. | | | | | | | | | |
| Steamed at 575 hr$^{-1}$ GHSV. This is equivalent to plant steam at 17,000 lb/Hr. | | | | | | | | | |
| 22 | 415 | 441 | 1.370 | 1500 | 138 | 69.6 | 61.7 | 43.0 | 72.2 |
| 30 | 415 | 444 | 1.320 | 1500 | 341 | 73.7 | 55.1 | 40.6 | 68.6 |

TABLE II

| Date | Temperature, °C. Salt | Temperature, °C. Hot Spot | Butane Feed Mole % | GHSV Hr$^{-1}$ | On-Stream Hrs. | Butane Conv. Mole % | MAN Select. Mole % | MAN Yield Mole % | MAN Yield Mole % |
|---|---|---|---|---|---|---|---|---|---|
| 1st Month | | | | | | | | | |
| 13 | 405 | 435 | 1.12 | 1500 | 25 | 77.1 | 43.2 | 33.3 | 56.3 |
| Treated with 1.2 ml PCl$_3$ in nitrogen over 10 min. at 405° C. | | | | | | | | | |
| 14 | 405 | 426 | 1.14 | 1500 | 44 | 54.1 | 45.0 | 24.4 | 41.2 |
| 20 | 410 | 432 | 1.182 | 1500 | 191 | 55.7 | 44.6 | 24.9 | 42.1 |
| 29 | 415 | 438 | 1.234 | 1500 | 404 | 61.3 | 44.8 | 27.5 | 46.5 |
| Steam treated at 415° C. for 2.0 hours. | | | | | | | | | |
| 2nd Month | | | | | | | | | |
| 2 | 417 | 428 | 1.318 | 1500 | 475 | 75.6 | 53.4 | 40.3 | 68.1 |
| 5 | 416 | 427 | 1.260 | 1500 | 547 | 75.2 | 49.0 | 36.9 | 62.4 |
| Steam treated at 415° C. for 2.0 hours. | | | | | | | | | |
| 6 | 405 | 415 | 1.227 | 1500 | 571 | 76.2 | 45.7 | 34.8 | 58.8 |
| Treated 5.0 ml PCl$_3$ in N$_2$ over 18 min. at 405° C. followed by 2.0 hour steaming. | | | | | | | | | |
| 8 | 421 | 426 | 1.258 | 1500 | 621 | 45.7 | 70.9 | 32.4 | 54.8 |
| 13 | 421 | 428 | 1.250 | 1500 | 740 | 64.3 | 69.5 | 44.7 | 75.5 |
| 18 | 421 | 445 | 1.220 | 1500 | 860 | 74.9 | 62.6 | 46.9 | 79.3 |
| 23 | 417 | 444 | 1.200 | 1500 | 980 | 76.5 | 60.8 | 46.6 | 78.8 |
| 25 | 415 | 439 | 1.06 | 1500 | 1028 | 75.7 | 59.8 | 45.2 | 76.4 |

(1) Catalyst removed from D202 prior to catalyst change - solid 3/16" × 3/16" tablets - 3' test unit.

TABLE III

| On-Stream Hrs. | Temperature, °C. Salt | Temperature, °C. Hot Spot | Butane Feed Mole % | GHSV Hrs.$^{-1}$ | Butane Conv. Mole % | MAN Select. Mole % | MAN Yield Mole % | MAN Yield Wt. % | Pressure PSIG Inlet | Pressure PSIG Exit | FIG. |
|---|---|---|---|---|---|---|---|---|---|---|---|
| 920 | 383 | 417 | 1.688 | 2500 | 77.4 | 64.6 | 50.0 | 84.5 | 20 | 15 | 1 |
| 1250 | 380 | 428 | 1.632 | 2500 | 78.1 | 64.5 | 50.4 | 85.2 | 20 | 15 | 3 |
| 1562 | 378 | 430 | 1.656 | 2500 | 78.1 | 60.2 | 47.0 | 79.4 | 20 | 15 | 3 |
| | | Treated with 10.5 ml Trimethyl Phosphite in air (500 Hr.$^{-1}$ GHSV) at 400° C. | | | | | | | | | |
| 1565 | 400 | 441 | 1.728 | 2500 | 85.0 | 51.6 | 43.8 | 74.0 | 20 | 15 | 4 |
| | | Steamed for 2.0 Hrs. (575 Hr.$^{-1}$ no air) at 400° C. | | | | | | | | | |
| 1568 | 400 | 405 | 1.712 | 2500 | 37.2 | 82.2 | 30.5 | 51.5 | 20 | 15 | 5 |
| | | Steamed as before for 4.0 Hrs. at 400° C. | | | | | | | | | |
| 1586 | 398 | 400 | 1.668 | 2500 | 33.0 | 80.7 | 26.7 | 45.1 | 20 | 15 | 6 |
| | | Steamed as before for 2.0 Hrs. at 410° C. | | | | | | | | | |
| 1590 | 410 | 450 | 1.711 | 2500 | 60.9 | 71.8 | 43.7 | 73.8 | 20 | 15 | 7 |
| 1616 | 415 | 465 | 1.526 | 2500 | 77.1 | 63.7 | 49.1 | 83.0 | 20 | 15 | 8 |

The invention claimed is:

1. In a process for the vapor phase oxidation of hydrocarbons having 4 carbon atoms to produce maleic anhydride comprising contacting said hydrocarbons with a fixed bed vanadium-phosphorus-oxygen catalyst, containing P:V in an atomic ration of ½ to 3:1 whereby said catalyst gradually decreases in selectivity, wherein the improvement comprises contacting sid catalyst with phosphorus compound of phosphorus halide, phosphorus oxyhalide, organic phospines, organic phospites, organic phosphates or mixtures thereof at a temperature in the range of about 0° to 600° C. and thereafter contacting said catalyst with a flow of stream at a temperature in the range of 300° to 600° C. in an amount and for a sufficient duration whereby said catalyst is regenerated.

2. The process according to claim 1 wherein said hydrocarbon is n-butane.

3. The process according to claim 1 wherein said contacting with said phosphorus compound is over an extended period of time prior to said contacting with steam.

4. The process according to claim 3 wherein said contacting with said phosphorus compound is substantially continuous.

5. The process according to claim 3 wherein said contacting with said phosphorus compound is intermittent.

6. The process according to claim 1 wherein said phosphorus compound contacting and said steam contacting are substantially contiguous.

7. The process according to claim 1 wherein said phosphorus compound contacting and steam contacting are repeated at intervals 8. The process according to claim 1 wherein said phosphorus compound is vaporous during said contacting.

9. The process according to claim 1 Wherein said phosphorus compound is inorganic.

10. The process according to claim 1 wherein said phosphorus compound is organic.

11. The process according to claim 1 wherein said phosphorus compound is an organo-phosphorus compund selected from the group consisting of:

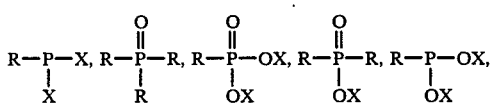

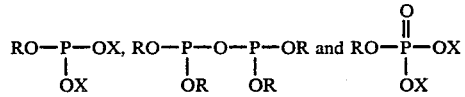

wherein R is phenyl or an alkyl radical of one to 6 carbon atoms and X is H or R.

12. The process according to claim 11 wherein said organo-phosphorus compound is trimethyl phosphite 13. The process according to claim 1 wherein said phosphorus compound is a phosphorus halide of the formula PX′$_n$ wherein X′ is Cl, Br, I or F and n is 3 to 5.

14. The process according to claim 13 wherein said phosphorus halide is PCl$_3$.

15. The process according to claim 1 wherein said phosphorus compound is an alkyl ester of phosphoric acid having the formula (R′O)$_3$P=O wherein R′ is hydrogen or an alkyl radical having one to six carbon atoms at least one R′ being an alkyl radical.

16. The process according to claim 15 wherein said ester is trimethyl phosphate

17. The process according to claim 1 wherein said hydrocarbon and phosphorus compound concurrently contact said catalyst.

18. The process according to claim 1 wherein said phosphorus compound contacts said catalyst in the absence of said hydrocarbon.

19. The process according to claim 1 wherein said hydrocarbon and steam concurrently contact said catalyst.

20. The process according to claim 1 wherein said steam contacts said catalyst in the absence of said hydrocarbon.

21. The process according to claim 1 wherein the activity of said catalyst is increased after said steam contacting.

22. In a process for the vapor phase oxidation of hydrocarobons having 4 carbon atoms to produce maleic anhydride comprising contacting said hydrocarbons with a fixed bed vanadium-phosphorus-oxygen catalyst containing P:V in an atomic ration of ½ to 3:1, said catalyst having been contacted with a phosphorus compund of phosphines, organic phosphites, organic phosphates or mixtures thereof at a temperature in the range of about 0° to 600° C. whereby said catalyst exhibits a first yield wherein the improvement comprises contacting said catalyst with a flow of steam at a temperature in the range of 300° to 600° C. in an amount and for sufficient duration such that said catalyst exhibits a second yield greater than said first yield.

23. The process according to claim 22 wherein the activity of said catalyst is increased after said steam contacting.

UNITED STATES PATENT AND TRADEMARK OFFICE
CERTIFICATE OF CORRECTION

PATENT NO. : 4,596,878  Page 1 of 2
DATED : 6/24/86
INVENTOR(S) : CLICK AND BARONE It is certified that error appears in the above—identified patent and that said Letters Patent is hereby corrected as shown below:

Col. 1, line 51 reads "$PCL_5$" but should read --- $PCl_5$ ---

Col. 4, line 21 reads ",hposphorus" but should read --- phosphorus ---

Col. 5, line 23 reads "o" but should read --- on ---

Col. 5, line 32 reads " V PZne" but should read --- $VPZn_e$ ---

Col. 5, line 33 reads "Sic Li Ox" but should read --- $Si_cLiO_x$ ---

Col. 5, line 34 reads "0.3 nd" but should read --- 0.3 and ---

Col. 6, line 13 reads "deposited" but should read --- be deposited ---

Col. 8, Line 6 reads "10 tc" but should read --- 1.0 to ---

Col. 9, line 65 reads "$R_2P(0)OX$" but should read --- $R_2P(O)OX$ ---

Col. 10, line 5 reads "$(RO_3)P$" but should read --- $(RO)_3P$ ---

Col. 12, line 36 reads "op imum" but should read --- optimum ---

Col. 12, line 37 reads "pilot cub" but should read --- pilot tube ---

UNITED STATES PATENT AND TRADEMARK OFFICE
CERTIFICATE OF CORRECTION

PATENT NO. : 4,596,878  
DATED : 6/24/86  
INVENTOR(S) : CLICK AND BARONE

Page 2 of 2

It is certified that error appears in the above-identified patent and that said Letters Patent is hereby corrected as shown below:

Col. 15 and 16, TABLE II headings, heading on right side reads
```
"man            but should read    --- man
yield                                  yield
mole %"                                wt %   ---
```

Col. 17, line 27, claim 1 reads "sid catalyst" but should read --- said catalyst ---

Col. 17, line 32, claim 1 reads "stream" but should read --- steam ---

Signed and Sealed this

Twenty-fourth Day of March, 1987

Attest:

Attesting Officer

DONALD J QUIGG

Commissioner of Patents and Trademarks